United States Patent
Higaki et al.

(10) Patent No.: US 10,080,593 B2
(45) Date of Patent: Sep. 25, 2018

(54) ROD TEMPLATE

(71) Applicant: NISHIJIMA MEDICAL CO., LTD., Aichi (JP)

(72) Inventors: Shigehiko Higaki, Aichi (JP); Tomohiro Ohtake, Aichi (JP); Masato Yokoyama, Aichi (JP)

(73) Assignee: NISHIJIMA MEDICAL CO., LTD., Aichi (JP)

( * ) Notice: Subject to any disclaimer, the term of this patent is extended or adjusted under 35 U.S.C. 154(b) by 0 days.

(21) Appl. No.: 15/434,329

(22) Filed: Feb. 16, 2017

(65) Prior Publication Data

US 2017/0238976 A1 Aug. 24, 2017

(30) Foreign Application Priority Data

Feb. 22, 2016 (JP) ................. 2016-031029

(51) Int. Cl.
| | |
|---|---|
| A61B 17/70 | (2006.01) |
| A61B 90/00 | (2016.01) |
| A61L 31/02 | (2006.01) |
| A61L 31/06 | (2006.01) |
| A61L 31/14 | (2006.01) |
| A61B 17/88 | (2006.01) |
| A61B 17/00 | (2006.01) |
| A61B 17/56 | (2006.01) |

(52) U.S. Cl.
CPC ...... *A61B 17/7083* (2013.01); *A61B 17/7011* (2013.01); *A61B 17/7032* (2013.01); *A61B 17/8863* (2013.01); *A61B 90/06* (2016.02); *A61L 31/022* (2013.01); *A61L 31/06* (2013.01); *A61L 31/14* (2013.01); *A61B 2017/00867* (2013.01); *A61B 2017/00907* (2013.01); *A61B 2017/568* (2013.01); *A61B 2090/061* (2016.02); *A61B 2090/067* (2016.02)

(58) Field of Classification Search
CPC ........ A61B 17/7002–17/7029; A61B 17/7083; A61B 17/8863
See application file for complete search history.

(56) References Cited

U.S. PATENT DOCUMENTS

| | | | | |
|---|---|---|---|---|
| 5,970,801 | A * | 10/1999 | Ciobanu | A61B 5/0876 73/861.52 |
| 6,221,077 | B1 * | 4/2001 | Rinner | A61B 17/8863 33/512 |
| 2011/0051212 | A1 * | 3/2011 | Rolland | A61B 5/0066 359/212.2 |
| 2011/0087170 | A1 * | 4/2011 | Insignares | A61B 17/3462 604/167.03 |
| 2016/0007976 | A1 * | 1/2016 | Gauthier | A61L 31/14 428/138 |

FOREIGN PATENT DOCUMENTS

JP 3593262 11/2004

* cited by examiner

*Primary Examiner* — Nicholas Plionis
(74) *Attorney, Agent, or Firm* — Wenderoth, Lind & Ponack, L.L.P.

(57) ABSTRACT

A rod template for determining a curvature and a length of a spinal rod used for joining vertebrae in a spine fusion surgery in advance includes a core, a transparent outer tube, and a transparent filler. The core is made of metal and includes a scale on a surface thereof. The outer tube is made of silicone rubber and covers the core. The filler is made of liquid silicone rubber and inserted in a gap between the outer tube and the core to fill the gap.

8 Claims, 14 Drawing Sheets

ROD TEMPLATE

CROSS REFERENCE TO RELATED APPLICATION

This application claims priority from Japanese Patent Application No. 2016-031029 filed on Feb. 22, 2016. The entire contents of the priority application are incorporated herein by reference.

TECHNICAL FIELD

The present disclosure relates to a tool for a spinal fusion surgery.

BACKGROUND

A spinal fusion surgery that is one type of spine surgery has been known. In the spinal fusion surgery, vertebrae are joined together with spinal rods. The spinal fusion surgery is for spinal stenosis, spinal disc herniation, scoliosis, spinal cord trauma, spondylolisthesis or other spinal disorders.

A rod template may be used in the spinal fusion surgery. The rod template may include a core and an outer tube that covers the core. The rod template is used for determining a curvature and a length of the spinal rods that are used for joining the vertebrae. The core includes scale marks on the surface thereof. The length of the spinal rods is determined based on a measurement with the scale marks. The outer tube is used for restricting small metal pieces from spreading if cracking of the surface of the core occurs when the rod template is bent and such small metal pieces are produced from the cracking.

The outer tube is made of transparent material so that the scale marks on the core are visible through the outer tube. The known rod template may include a gap between the core and the outer tube. The gap may decrease visibility of the scale marks.

SUMMARY

The present invention was made in view of the foregoing circumstances. An object is to improve visibility of scale marks on a surface of a core of a rod template inserted in an outer tube.

A rod template for determining a curvature and a length of a spinal rod used for joining vertebrae in a spine fusion surgery in advance includes a core, a transparent outer tube, and a transparent filler. The core is made of metal and includes a scale on a surface thereof. The outer tube is made of silicone rubber and covers the core. The filler is made of liquid silicone rubber and inserted in a gap between the outer tube and the core to fill the gap.

According to technologies described herein, the visibility of the scale marks on the surface of the core of the rod template inserted in the outer tube improves.

DETAILED DESCRIPTION

Figure 1:
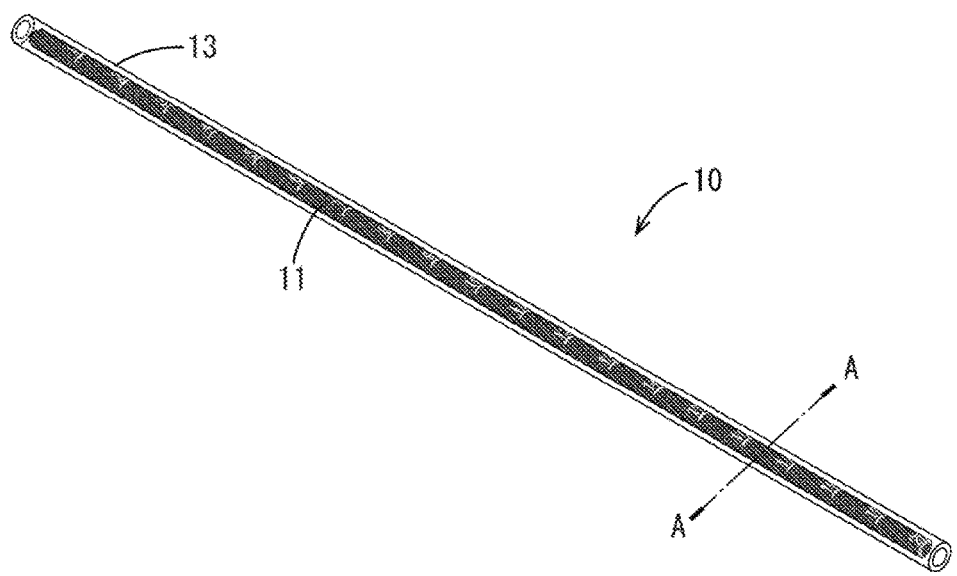
FIG. 1 is a perspective view of a rod template according to an embodiment.
Figure 2:
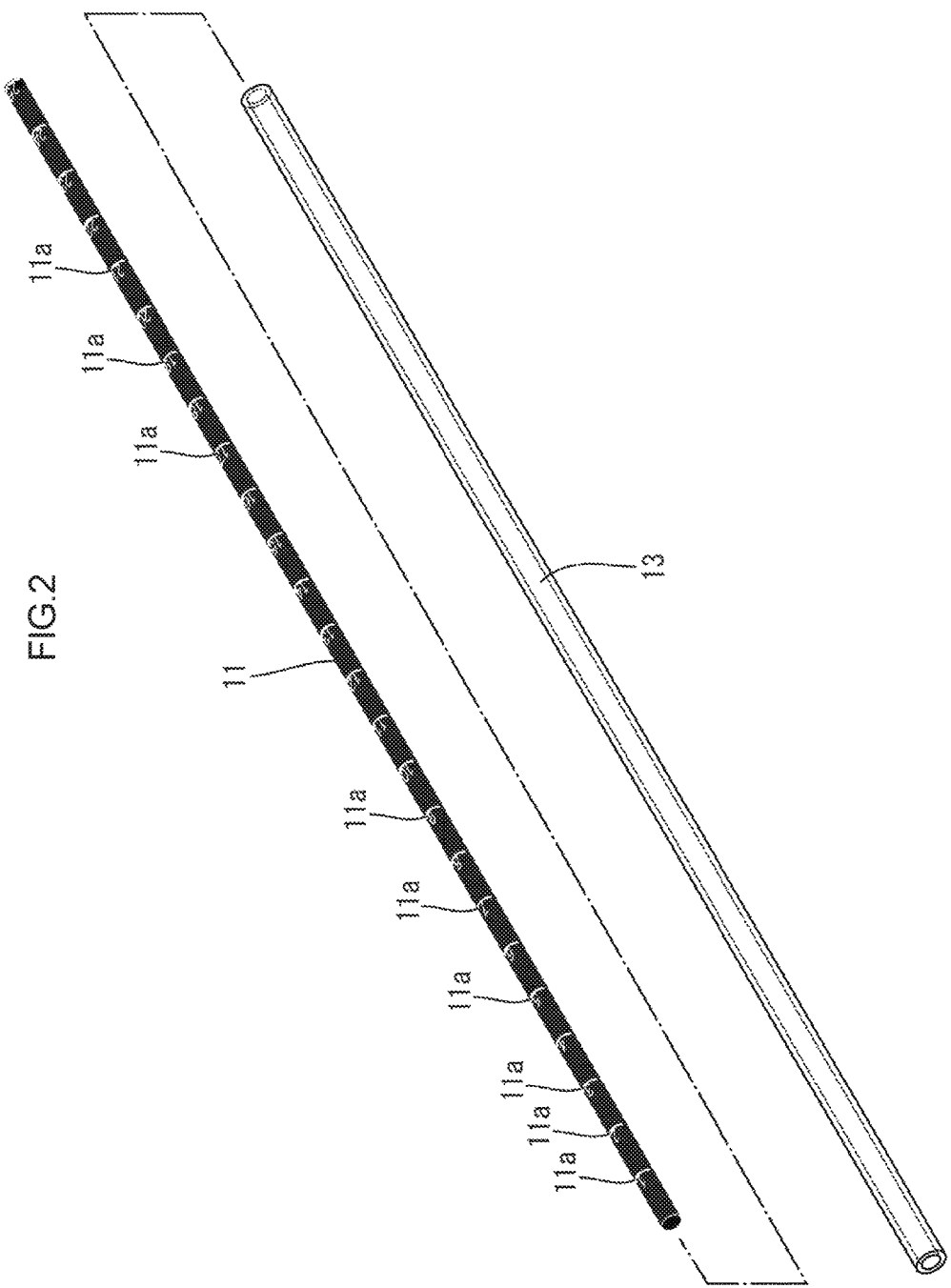
FIG. 2 is an exploded perspective view of the rod template.
Figure 3:
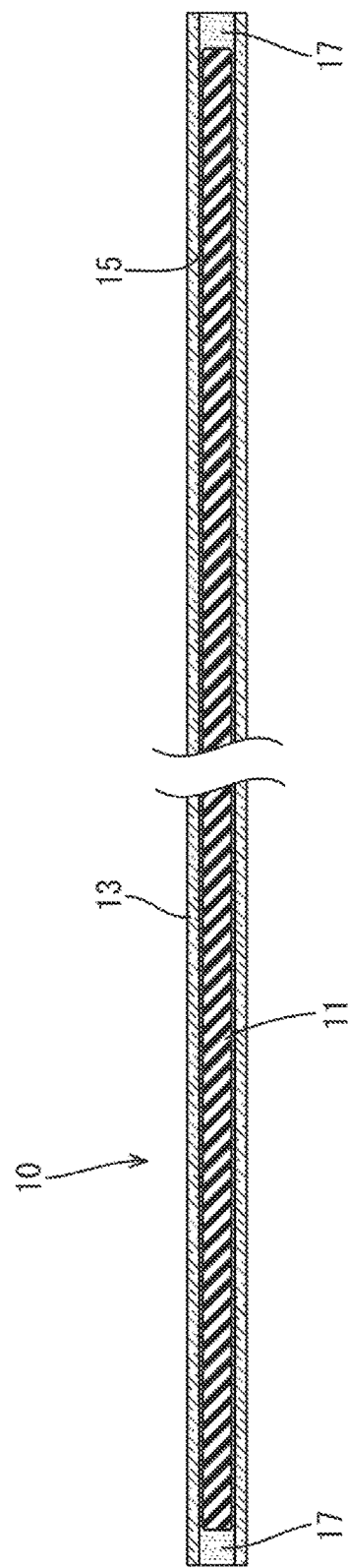
FIG. 3 is a cross-sectional view of the rod template cut along a horizontal direction.
Figure 4:
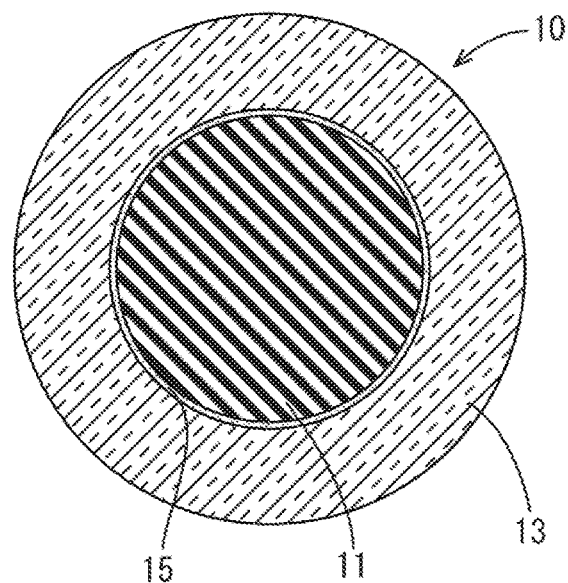
FIG. 4 is a cross-sectional view of the rod template cut along line A-A in FIG. 1.

An embodiment will be described according to FIGS. 1 to 14.

1. Configuration of Rod Template

A rod template 10 is a surgical tool for spinal fusion surgery. The rod template 10 is used for determining a curvature and a length of spinal rods 81 in advance. The spinal rods 81 are for joining vertebrae together in the spinal fusion surgery. The rod template 10 includes a core 11 that is a metal rod, an outer tube 13, a filler 15, and sealers 17.

The core 11 is made of aluminum or aluminum alloy. The reason why the core 11 is made of aluminum or aluminum alloy is that an aluminum material is a soft metal material and thus the core 11 can be made more flexible and easier to deform in comparison to other metal material. The flexibility that the core 11 has allows the core 11 to be deformed into different shapes. An alumite treatment is performed on the core 11 to reduce corrosion. The surface of the core 11 is colored in black. The color of the surface of the core 11 is not limited to black. The surface of the core 11 may be colored other than black. The core 11 includes scale marks 11a on the surface. The scale marks 11a are at equal intervals in the axial direction. The scale marks 11a are formed on the surface of the core 11 by scribing or printing.

The outer tube 13 is made of colorless and transparent biocompatible material, specifically, silicone rubber that is a material used for artificial blood vessels. The outer tube 13 covers and protects the core 11. The outer tube 13 restricts small metal pieces from spreading if the surface of the core 11 cracks and such small metal pieces are produced when the rod template 10 is deformed. The outer tube 13 may have an outer diameter of 5 mm and an inner diameter of 3 mm. The core 11 may have a diameter of 3 mm. Silicone is a polymer including synthetic compound made up of repeating units of siloxane.

The filler 15 is made of liquid silicone rubber. The liquid silicone rubber is a kind of rubber having a property to turn into an elastomer with cross-links at a temperature in a range from room temperature to about 60° C., which is a relatively low temperature range. Before cross-lining occurs, the liquid silicone rubber has low viscosity and shows flowability. There are room-temperature curing-type and thermosetting-type liquid silicone rubbers classified according to response temperatures. The filler 15 in this embodiment is a room-temperature curing-type liquid silicone rubber, specifically, a one-component condensed-type room temperature vulcanizing (RTV) silicone rubber. The term "one-component" refers to a component including a base agent and a curing agent (a cross-linking agent) therein. The term "condensed-type" refers to a type that the curing agent (the cross-linking agent) is activated by moisture in the air and reaction progresses.

The filler 15 is inserted in the outer tube 13 to fill a gap between the inner surface of the outer tube 13 and the outer surface of the core 11. The filler 15 is colorless and transparent, similarly to the outer tube 13. The reason why the rubber is used for the outer tube 13 and the filler 15 is to restrict the outer tube 13 and the filler 15 from breaking when the core 11 is deformed. The outer tube 13 has flexibility that allows the outer tube 13 to curve along the core 11 together with the filler 15 when the rode template 10 is deformed into a different shape.

The sealers 17 are disposed at ends of the outer tube 13, respectively, to seal the ends of the outer tube 13. The sealers 17 are made of the liquid silicone rubber.

The rod template 10 is produced as follows. The filler 15 is applied to an entire surface of the core 11. The core 11 with the filler 15 on the surface of the core 11 is inserted in the outer tube 13. The filler 15 hardens at the room temperature in response to the moisture in the air and turned into a transparent elastomer. The filler 15 is integrated with the outer tube 13 in the process of curing. The filler 15 forms a transparent filling layer with which the gap between the outer tube 13 and the core 11 is filled (see FIGS. 4 and 5).

After the core 11 is inserted in the outer tube 13, the sealers 17 are fitted in the ends of the outer tube 13 from the outside. The fillers 17 harden in response to the moisture in the air and form sealing layers at the ends of the outer tube 13. Then, the rod template 10 is complete.

2. Relationship Between the Filler 15 and the Visibility of the Scale Marks 11

Figure 6:
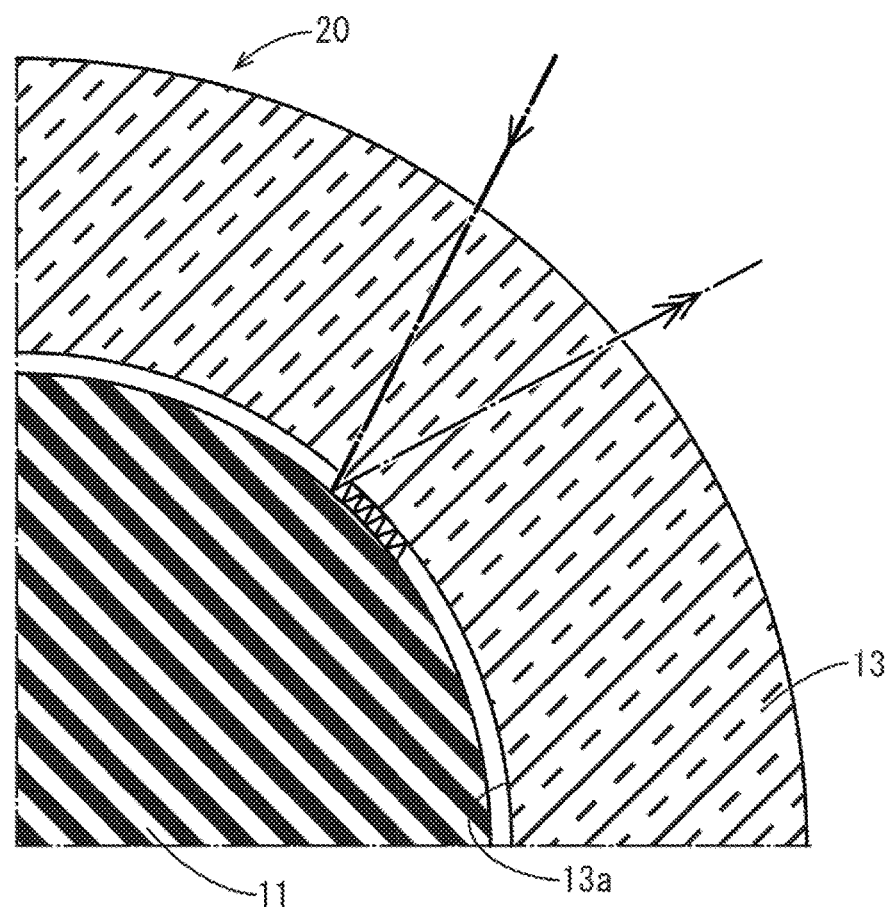
FIG. 6 is a magnified cross-sectional view of a portion of a rod template, which is a comparative example, cut along a vertical direction.

A rod template 20 illustrated in FIG. 6 is an example comparative to the rod template 10. The rod template 20 includes a core 11 and an outer tube 13 having the same configuration as those of the core 11 and the outer tube 13 of the rod template 10. The rod template 20 does not include the filler 15 (or a filling layer), that is, a gap remains between the outer tube 13 and the core 11 without being filled.

As indicated with an arrow in FIG. 6, some rays of light reflected off the surface of the core 11 are reflected by the inner surface 13a of the outer tube 13 because the gap remains between the outer tube 13 and the core 11. Therefore, the rays of light are less likely to pass through the outer tube 13. Because a smaller amount of light reaches viewer's eyes in comparison to the rode template 10, the visibility of the scale marks 11a on the core 11 is more likely to decrease.

Figure 5:
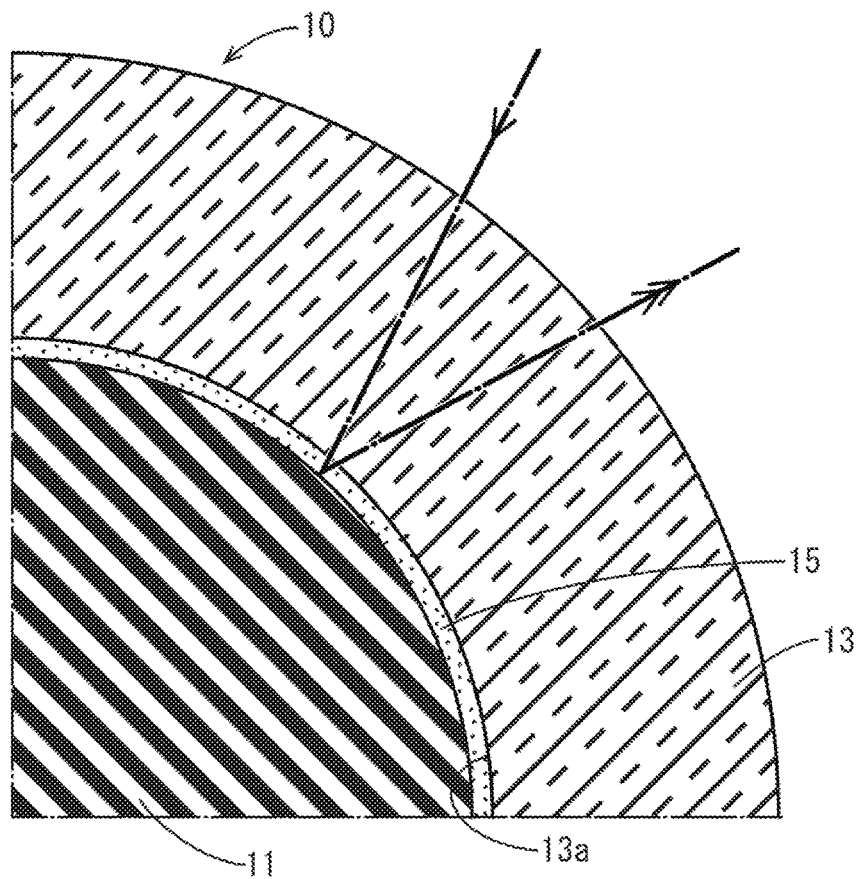
FIG. 5 is a magnified cross-sectional view of a portion of the rod template cut along a vertical direction.

As illustrated in FIG. 5, the rod template 10 includes the filler 15 (the filling layer) with which the gap between the outer tube 13 and the core is filled. Furthermore, the filler 15 and the outer tube 13 are made of the silicone rubbers including silicone polymers as base components. Namely, the base components of the filler 15 and the outer tube 13 are the same kind of base components.

With the filler 15 including the same base component as that of the outer tube 13, refractive indexes of the outer tube 13 and the filler 15 are about equal to each other. Furthermore, the filler 15 integrates with the outer tube 13 as the filler 15 hardens. As illustrated in FIG. 5, some rays of light reflected off the surface of the core 11 are less likely to be reflected by the inner surface 13a of the outer tube 13. Namely, the rays of light are more likely to be passed through the outer tube 13. A larger amount of light reaches the viewer's eyes and thus the visibility of the scale marks 11a improves.

3. Example of Spine Fusion Surgery

Figure 7:
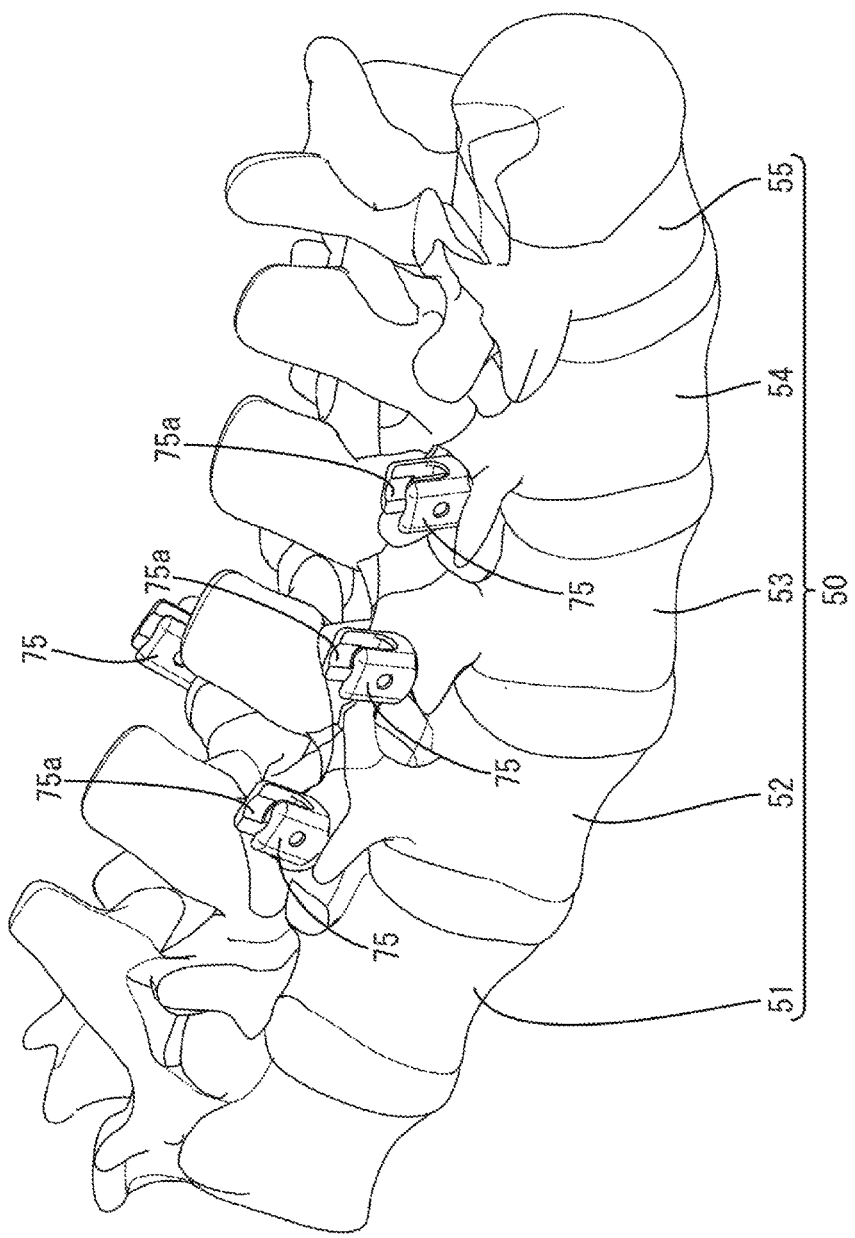
FIG. 7 is a diagram illustrating a state of a spinal fusion surgery.
Figure 8:
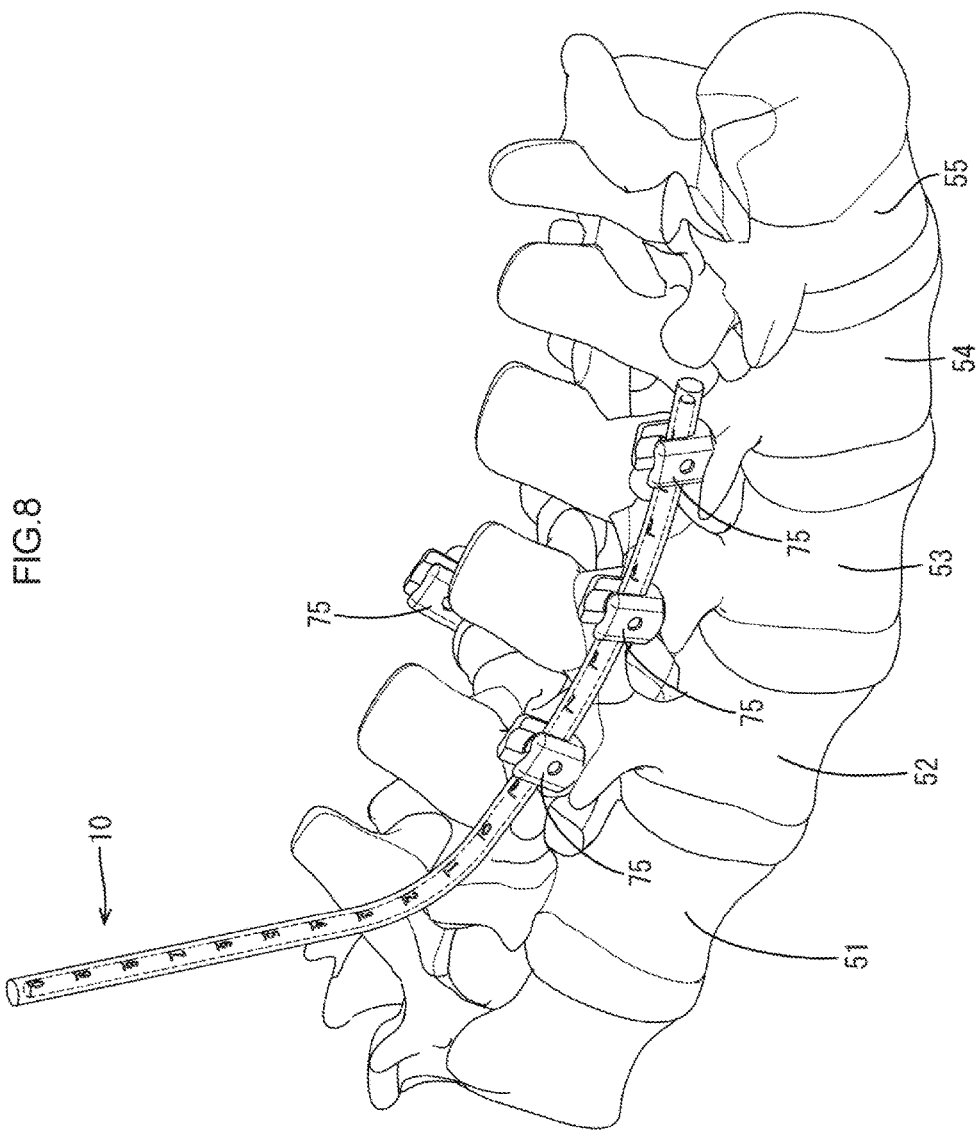
FIG. 8 is a diagram illustrating a state of the spinal fusion surgery.
Figure 9:
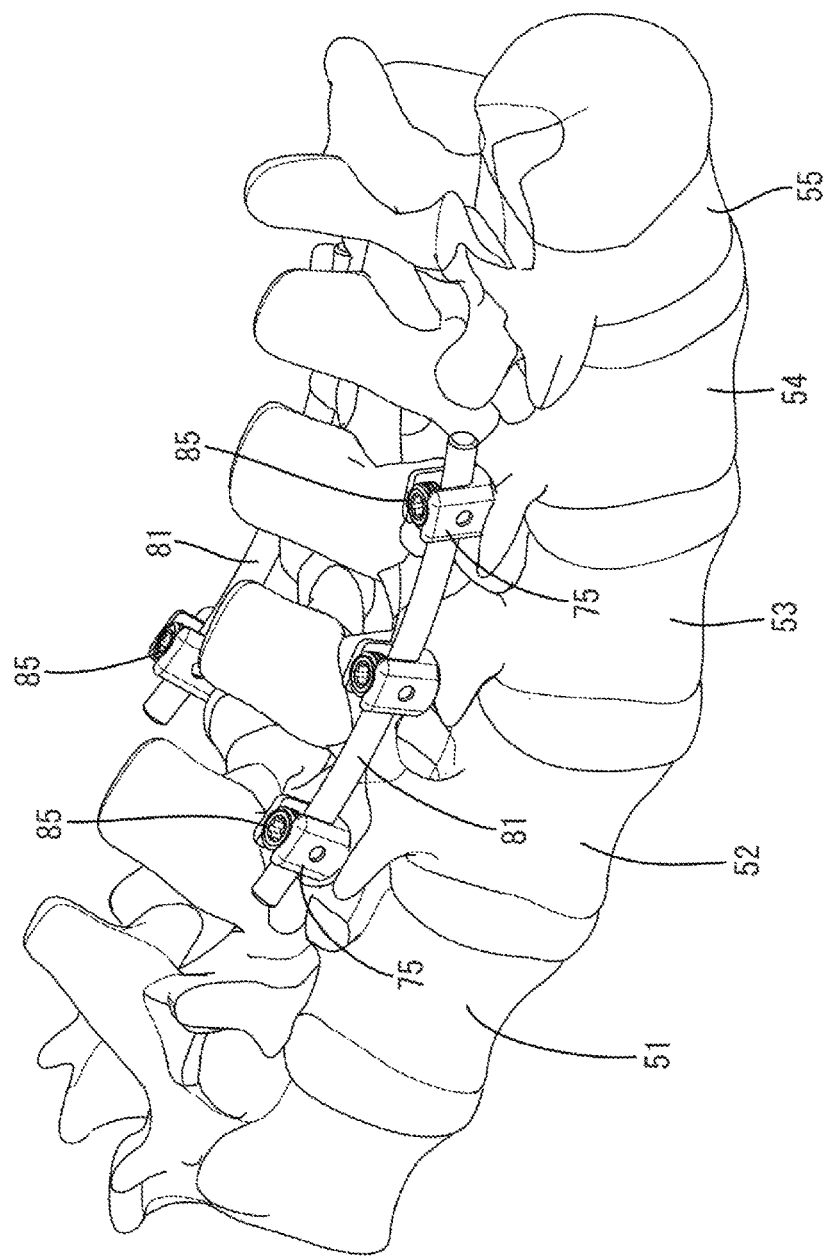
FIG. 9 is a diagram illustrating a state of the spinal fusion surgery.
Figure 10:
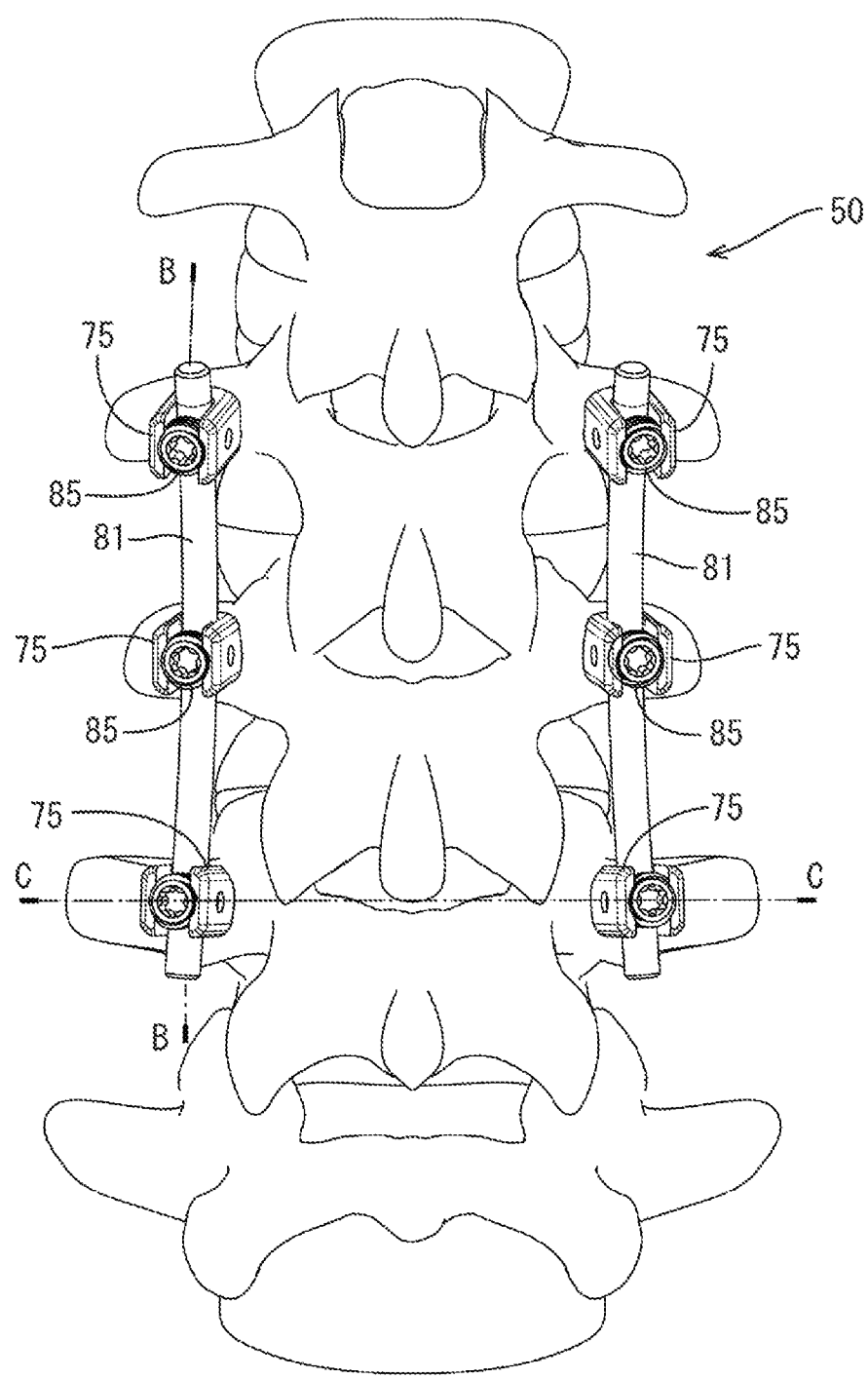
FIG. 10 is a front view of a spine after the spinal fusion surgery.
Figure 11:
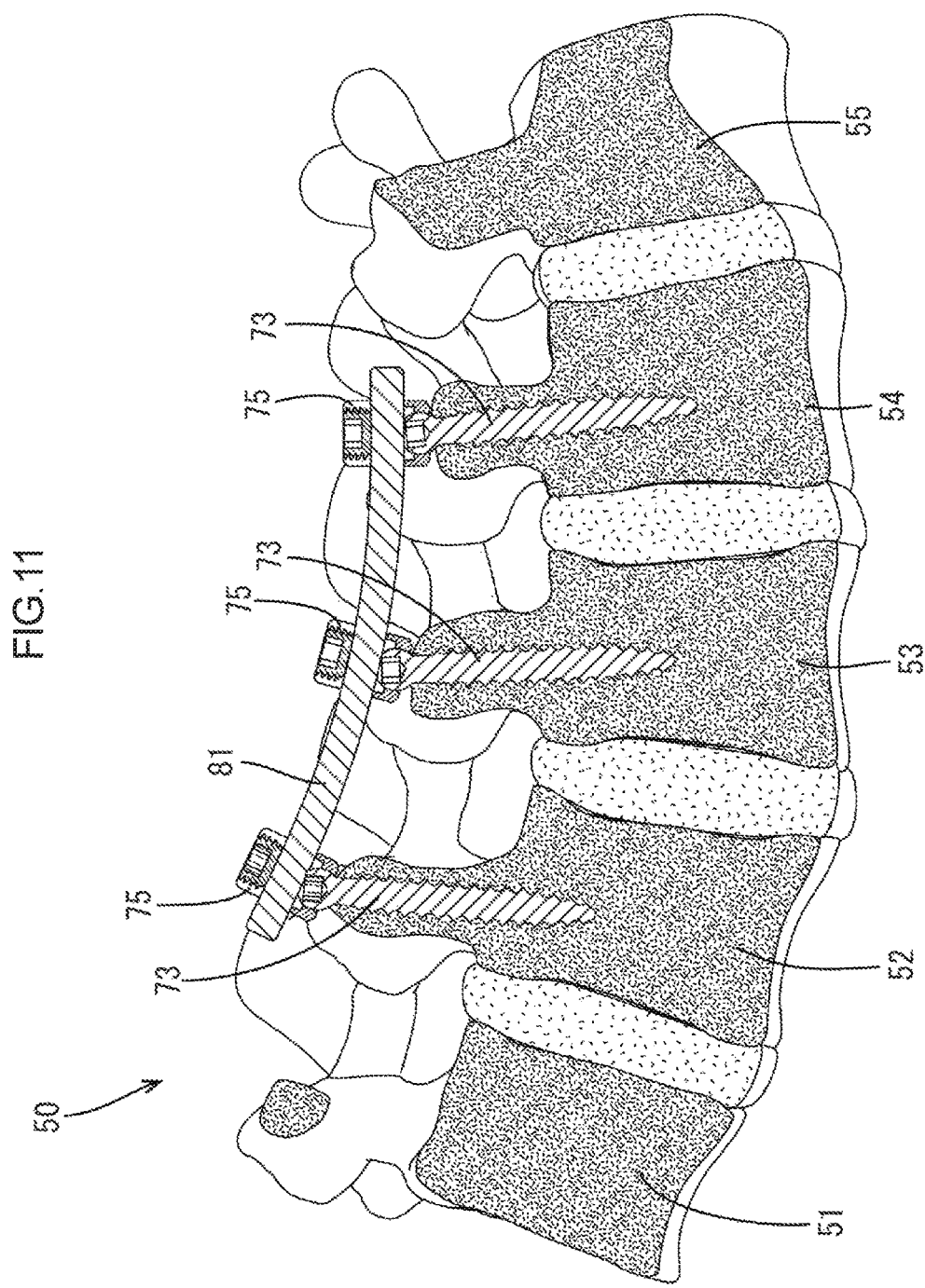
FIG. 11 is a cross-sectional view of the spine along line B-B in FIG. 10.

As illustrated in FIGS. 7 to 9, a lumber spine 50 includes the first lumber vertebra 51, the second lumber vertebra 52, the third lumber vertebra 53, the fourth lumber vertebra 54, and the fifth lumber vertebra 55.

The spine fusion surgery is for joining some of the lumber vertebrae 51 to 55 with spinal rods 81. A procedure of the spine fusion surgery for joining the second lumber vertebra 52 through the fourth lumber vertebra 54 will be described below.

Figure 13:
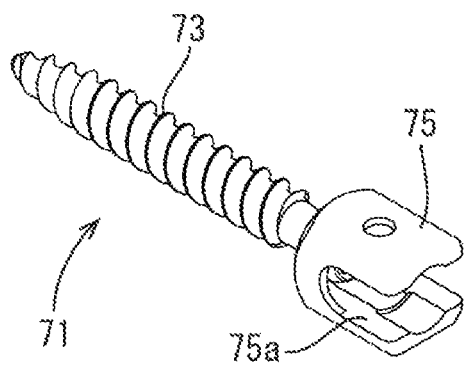
FIG. 13 is a perspective view of a screw.

In the spine fusion surgery, screws 71 are fixed to the target vertebrae of the lumber spine 50. The screws 71 are made of titanium alloy or unalloyed titanium. As illustrated in FIG. 13, each screw 71 includes a shank 73 and a head 75. The head 75 includes a holding portion 75a for holding the spinal rod 81. The holding portion 75a includes a U-shaped groove.

Figure 12:
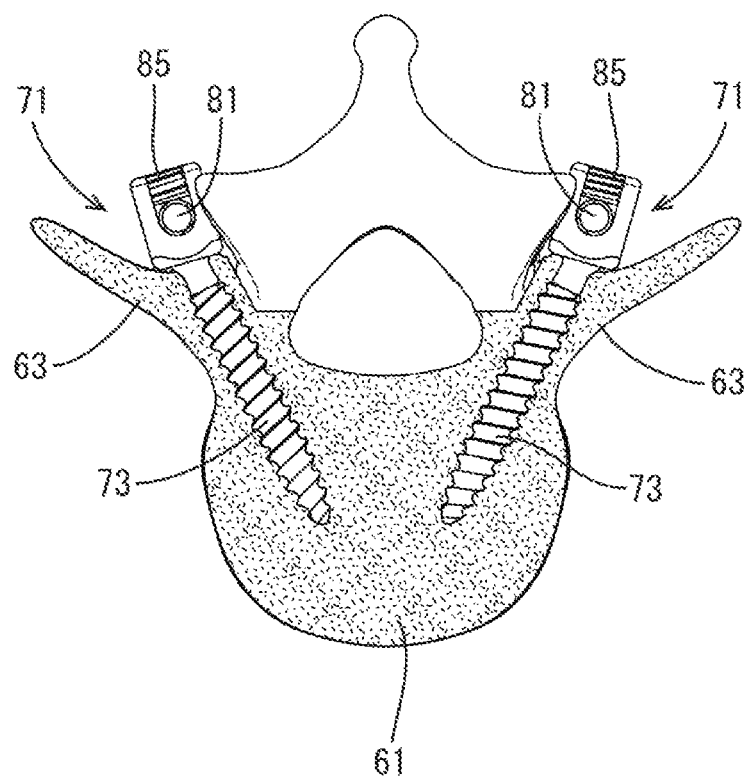
FIG. 12 is a cross-sectional view of the spine along line C-C in FIG. 10.

Specifically, as illustrated in FIG. 7, the screws 71 are fixed to the second lumber vertebra 52 through the fourth lumber vertebra 54 on the right side and the left side. As illustrated in FIG. 12, two screws 71 are screwed into each of the lumber vertebrae 52 through 54 from pedicles of vertebral arches 63 to a vertebral body 61.

After the screws 71 are fixed, determination of a curvature and a length of the spinal rods 81 is performed using the rod template 10. The curvature and the length of the spinal rods 81 are determined in advance to the joining of the lumber vertebrae 52 through 54. Specifically, as illustrated in FIG. 8, the rod template 10 is bent to be fitted in the holding portions 75a of the screws 71 that are fixed to the second lumber vertebra 52 through the fourth lumber vertebra 54, the positions of which are corrected to proper positions. Furthermore, the length of the spinal rods 81 corresponding to a length from the second lumber vertebra 52 through the fourth lumber vertebra 54 is determined in advance according to reading of the scale marks 11a on the rod template 10. In FIG. 8, the core 11 is in white for an illustration purpose. However, the actual color of the core 11 is black.

The spinal rods 81 are made of titanium alloy or unalloyed titanium. The spinal rods 81 are straight before processed. The spinal rods 81 are bent by a bending machine (not illustrated) into a shape corresponding to the shape of the rod template 10. Then, the spinal rods 81 are cut in the length determined in advance using the rod template 10.

Figure 14A:
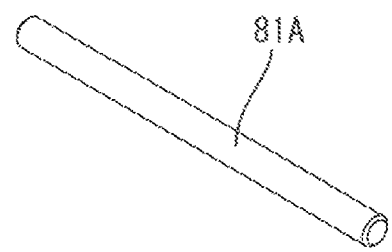
FIG. 14A is a perspective view of an unprocessed spinal rod.
Figure 14B:
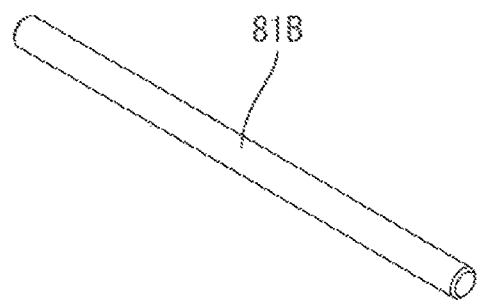
FIG. 14B is a perspective view of an unprocessed spinal rod.
Figure 15:
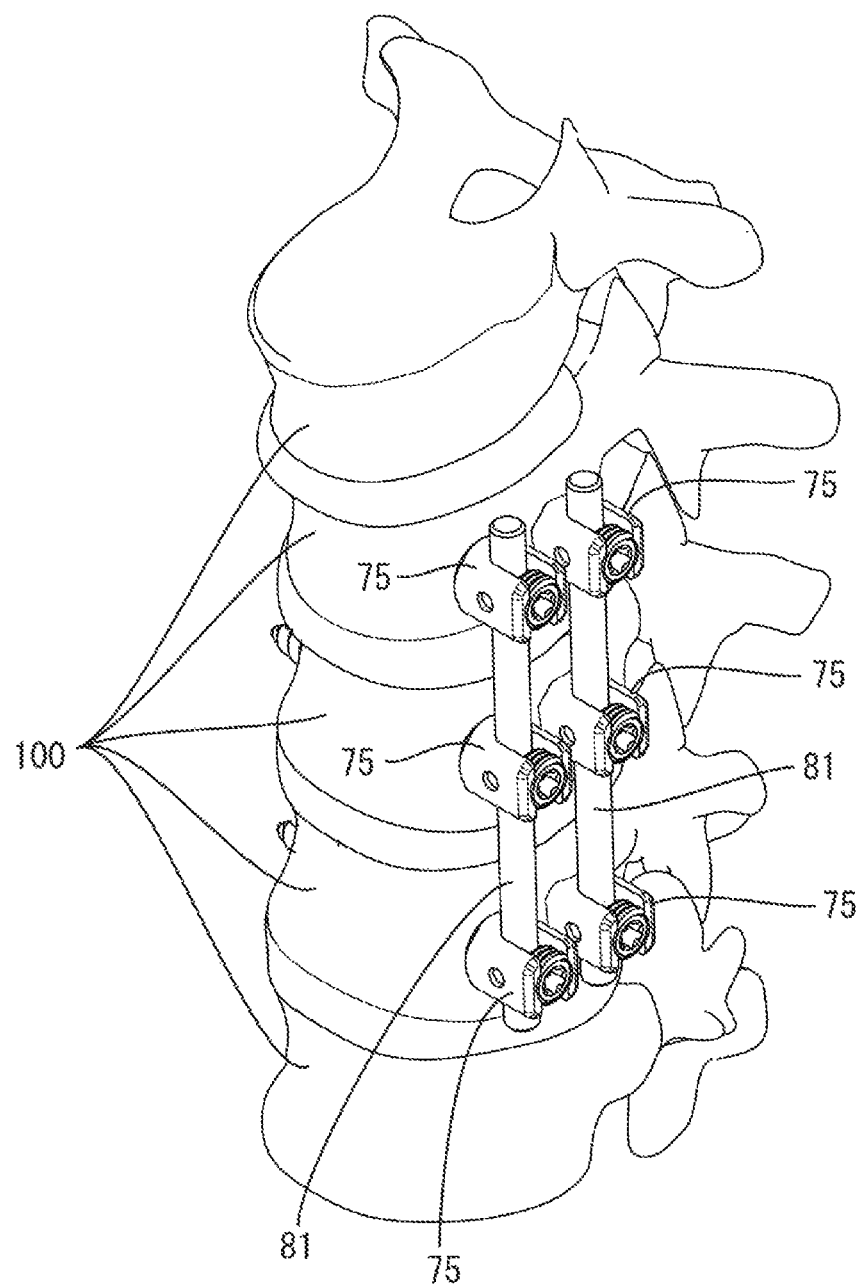
FIG. 15 is a perspective view of a thoracic spine after a spinal fusion surgery according to another embodiment.
Figure 16:
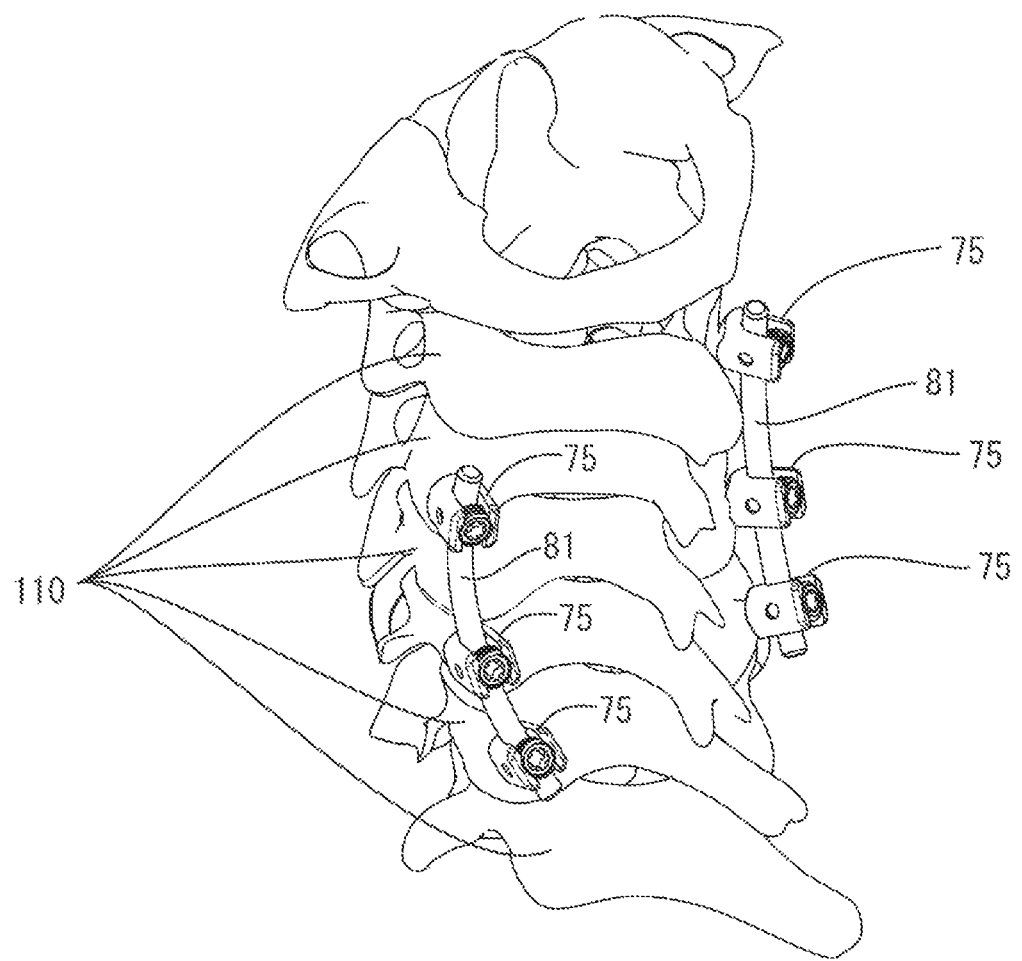
FIG. 16 is a perspective view of a cervical spine after a spinal fusion surgery according to another embodiment.

Two spinal rods 81 are used for fixing the right side and the left side of the lumber spine 50. Two spinal rods 81 are prepared for fixing the right side and the left side of the lumber spine 50. As illustrated in FIGS. 14A and 14B, spinal rods 81A and 81B having different lengths are prepared. The spinal rods 81A or the spinal rods 81B having the length closer to the length determined using the rod template 10 are used as the spinal rods 81.

As illustrated in FIG. 9, the spinal rods 81 are fitted in the holding portions 75a of the screws 71 fixed to the second lumber vertebra 52 through the fourth lumber vertebra 54. Plugs 85 are fixed to the holding portion 75a of the screws 71. The plugs 85 are screwed into the holding portions 75a and fixed.

With the plugs 85 fixed to the holding portion 75a, the spinal rods 81 are less likely to be removed from the holding portions 75a. This procedure is performed on the both sides of the lumber spine 50. As a result, the second vertebra 52 through the fourth lumber vertebra 54 are joined with the spinal rods 81.

4. Advantageous Effects

The rod template 10 has a configuration including the gap that is filled with the filler 15 between the outer tube 13 and the core 11. The filler 15 and the outer tube 13 are made of the silicone rubbers including the silicone polymers as the base components. Namely, the base components of the filler 15 and the outer tube 13 are the same. As illustrated in FIG. 5, some rays of light reflected off the surface of the core 11 are less likely to be reflected by the inner surface of the outer tube 13 and thus more rays of light are passed through the outer tube 13. Therefore, the larger amount of light reaches the view's eyes. According to the configuration, the visibility of the scale marks 11a improves.

The filler 15 is made of the liquid silicone rubber having the flowability in the state before reacted to the moisture in the air. With the filler 15, friction between the core 11 and the outer tube 13 decreases and the core 11 can be smoothly inserted into the outer tube 13. Therefore, the core 11 is easily fitted in the outer tube 13.

OTHER EMBODIMENTS

The scope of the present invention is not limited to the above embodiment. The following embodiments may be included in the scope of the present invention.

(1) The technology described herein can be applied to a thoracic spine 100 illustrated in FIG. 13 and a cervical spine 110 illustrated in FIG. 14.

(2) The filler 15 may be made of two-component condensed-type RTV silicone rubber. The filler 15 may be made of any liquid silicone rubbers including a thermosetting liquid silicone rubber.

(3) The core 11 may be made of any plastically deformable metal materials, for example, stainless steel. The core 11 may be made of shape-memory alloy such as nickel titanium (Ni—Ti) alloy. Because the shape-memory alloy recovers its original shape when the shape-memory alloy is heated to a shape recovery temperature, it is preferable to use the shape-memory alloy for the rod template 10 that is repeatedly used. Namely, because the deformed rod template 10 recovers its original shape through heating, it is not necessary to manually reshape the rod template 10. Furthermore, the rod template 10 is cleaned after use and a high-pressure steam sterilizing process (an autoclave sterilizing process) may be performed on the cleaned rod template 10. If the shape recovery temperature is set below a sterilizing temperature at which the high-pressure steam sterilizing process is performed, the recovery of the shape of the rod template 10 can be complete in the sterilizing process. If the shape recovery temperature is set equal to the sterilizing temperature, whether a temperature of the steam is increased to a target temperature can be determined based on whether the rod template 10 recovers its original shape. Namely, if the original shape of the rod template 10 is observed, it can be assumed that the temperature of the steam has reached the target temperature.

(4) The sizes of the outer tube 13 and the core 11 are not limited to those described above. Furthermore, the outer tube 13 can be tinted as long as the outer tube 13 is transparent.

(5) The filler 15 may not be transparent before the filler 15 is cured. The filler 15 can be tinted as long as the filler 15 is transparent when the filler 15 is cured.

The invention claimed is:

1. A rod template for determining a curvature and a length of a spinal rod used for joining vertebrae in a spine fusion surgery in advance to the joining of the vertebrae, the rod template comprising:
   a transparent outer tube made of silicone rubber, the transparent outer tube having an opening at least one end and a hollow portion defined by an inner surface of the transparent outer tube that communicates with the opening;
   a core made of metal and including scale marks on a surface thereof, the core being disposed in the hollow portion of the transparent outer tube with a gap between the inner surface of the transparent outer tube and the core; and
   a transparent filler made of liquid silicone rubber that completely fills the gap between the inner surface of the transparent outer tube and the core,
   wherein the hollow portion of the transparent outer tube has a length that is equal to or greater than a length of the core.

2. The rod template according to claim 1, wherein the core is made of shape-memory alloy.

3. The rod template according to claim 1, wherein
   the transparent filler is made of liquid silicone rubber that hardens at room temperature in response to moisture in air and integrates with the transparent outer tube as the transparent filler hardens,
   the core has flexibility that allows the core to be deformed into different shapes, and
   the transparent outer tube has flexibility that allows the transparent outer tube to curve along the core together with the transparent filler.

4. The rod template according to claim 3, wherein the liquid silicone rubber of the transparent outer tube and the liquid silicone rubber of the transparent filler include the same kind of base components.

5. The rod template according to claim 4, wherein the transparent outer tube and the transparent filler have refractive indexes about equal to each other.

6. The rod template according to the claim 4, wherein the base components of the liquid silicone rubber of the transparent outer tube and the liquid silicone rubber of the transparent filter are silicone polymers.

7. The rod template according to claim 1, wherein an outer diameter of the transparent outer tube is 5 mm and a diameter of the core is 3 mm.

8. The rod template according to claim 1, wherein the gap between the inner surface of the transparent outer tube and the core continuously extends the length of the core.

* * * * *